(12) United States Patent
Chang

(10) Patent No.: US 7,445,379 B2
(45) Date of Patent: Nov. 4, 2008

(54) DEVICE FOR MEASURING HEAT TRANSFER CHARACTERISTICS OF FLUID MATERIAL

(75) Inventor: Chun-Yi Chang, Tu-Cheng (TW)

(73) Assignee: Hon Hai Precision Industry Co., Ltd., Tu-Cheng, Taipei Hsien (TW)

( * ) Notice: Subject to any disclaimer, the term of this patent is extended or adjusted under 35 U.S.C. 154(b) by 173 days.

(21) Appl. No.: 11/473,281

(22) Filed: Jun. 21, 2006

(65) Prior Publication Data

US 2007/0086504 A1    Apr. 19, 2007

(30) Foreign Application Priority Data

Oct. 13, 2005    (CN)    ......................... 2005 1 0100385

(51) Int. Cl.
*G01N 25/20* (2006.01)
*G01N 25/18* (2006.01)
*G01K 1/00* (2006.01)

(52) U.S. Cl. ............................. 374/43; 374/44; 374/142

(58) Field of Classification Search .................. 374/43, 374/44, 29, 142
See application file for complete search history.

(56) References Cited

U.S. PATENT DOCUMENTS

| 4,154,099 | A | * | 5/1979 | Blu et al. ........................ 374/43 |
| 5,101,658 | A | * | 4/1992 | Wilson et al. ............... 73/61.62 |
| 5,756,878 | A | * | 5/1998 | Muto et al. ................. 73/25.03 |
| 5,988,875 | A | * | 11/1999 | Gershfeld et al. ............. 374/10 |
| 6,361,204 | B1 | | 3/2002 | Marzoli et al. |
| 6,550,961 | B1 | * | 4/2003 | Ueda ............................ 374/44 |
| 2006/0062273 | A1 | * | 3/2006 | Egolf et al. ..................... 374/44 |
| 2007/0223558 | A1 | * | 9/2007 | Lopez et al. ................... 374/44 |
| 2007/0288193 | A1 | * | 12/2007 | Lima ........................... 702/136 |

FOREIGN PATENT DOCUMENTS

JP    55107944 A    *    8/1980

\* cited by examiner

*Primary Examiner*—Edward Lefkowitz
*Assistant Examiner*—Mirellys Jagan
(74) *Attorney, Agent, or Firm*—Andrew C. Cheng

(57) ABSTRACT

A device includes a measuring assembly, a fluid pressure assembly, and a manometer. The measuring assembly includes a heating member defining a first contact surface, a cooling member defining a second contact surface facing the first contact surface, a platform, and a sleeve. The sleeve is configured far hermetically adjoining the heating and cooling members and allowing movement of the heating and cooling members relative to each other. The sleeve and the first and second contact surfaces form a cavity for receiving fluid material to be measured. The platform is configured for controlling the relative movement of the heating and cooling members to adjust the length of the cavity. The fluid pressure assembly is configured for compressing the fluid material into the cavity. The manometer is disposed on the sleeve or the fluid pressure assembly and is configured for detecting a fluid pressure of the fluid material in the cavity.

15 Claims, 2 Drawing Sheets

DEVICE FOR MEASURING HEAT TRANSFER CHARACTERISTICS OF FLUID MATERIAL

TECHNICAL FIELD

The present invention relates to measuring devices for heat transfer characteristics and, more particularly, to a device for measuring heat transfer characteristics of a fluid material.

BACKGROUND

At present, fluid materials such as liquid, mixtures of different liquids, mixtures of liquids and solids or gases, colloids, or gels are increasingly used as thermal media in numerous heating and/or cooling systems. In general, heat transfer characteristics, for example, thermal conductivity, of the fluid materials are physical properties which can be used to evaluate thermal efficiencies of the heating and/or cooling systems. The heat transfer characteristics of the fluid materials largely depend on their composition, mixing condition of ingredients and other factors, and are difficult to predict from the properties of their additives. Thus, measurement of the heat transfer characteristics is essential for using the fluid materials.

Many devices for measuring the heat transfer characteristics of the fluid materials typically use various types of detectors including a Wheatstone bridge with a metal filament coupled to one leg of the Wheatstone bridge. The metal filament is placed in a cavity through which the sample to be measured is passed. The practical implementation of such apparatuses, however, has encountered serious problems, such as drift in the voltage that controls current in the metal filament and serious inaccuracies in the results when even small variations occur in the temperature of the sample or in the temperature of the cavity. In order to ensure accuracy and credibility, the metal filament needs to be replaced frequently, but metal filaments can be very expensive because of the requirement for low reactivity and linearity of the voltage-temperature response.

Some devices are used for measuring the heat transfer characteristics of colloid by fastening a colloid between a heating block and a cooling block at a predetermined pressure. The two blocks each define a number of orifices each receiving a thermal probe therein, for measuring temperature of the respective locations in the block where each thermal probe is positioned. Generally, the predetermined pressure is maintained at a constant level during measurement in order to ensure constant contact between the colloid and the two blocks. Thus, based on the predetermined pressure, the thermal resistance and the thermal conductivity of the colloid can be respectively calculated from the equations (1) and (2) as follows:

$$R = \frac{(T_1 - T_2)}{Q}, \quad (1)$$

$$K = \frac{Q \times L}{A \times (T_1 - T_2)}, \quad (2)$$

Accordingly, a relationship equation (3) between the thermal resistance and the thermal conductivity can be deduced from the two equations (1) and (2) above as follows:

$$R = \frac{L}{A \times K}, \quad (3)$$

wherein R is thermal resistance between the two blocks; $T_1$ and $T_2$ are interface temperatures of the heating block and the cooling block respectively, Q is heat flux transferred to the colloid, L is heat transfer distance (i.e. thickness) of the colloid, A is cross sectional area in the heat transfer direction, and K is thermal conductivity of the colloid.

In the equations above, $T_1$ and $T_2$ can be detected via the thermal probes, Q can be obtained via the output power of the heating block, L and A can be directly obtained from the thickness and the cross sectional area of the colloid. As such, the R and K can be calculated from the equations above. Nevertheless, the colloid is prone to seep out of the interspace defined by the two blocks. This can result in an inaccurate determination of the thicknesses of the colloid.

In order to overcome shortcomings set out above, a gasket is applied between the two blocks for preventing the colloid from seeping out of the interspace defined by the two blocks. However, the gasket creates uneven pressure over the surfaces fastening the colloid so that contact status of the colloid with the two blocks can be inaccurately determined. That is, the gasket can make actual heat transfer characteristics difficult to measure.

What is needed, therefore, is a device for measuring heat transfer characteristics of a fluid material with relatively high accuracy.

What is also needed, therefore, is a method for measuring heat transfer characteristics of a fluid material.

SUMMARY

In accordance with an exemplary embodiment, a device includes a measuring assembly, a fluid pressure assembly, and a manometer. The measuring assembly includes a heating member defining a first contact surface, a cooling member defining a second contact surface, a platform, and a sleeve. The second contact surface is disposed facing the first contact surface. The sleeve is configured for joining the heating member and the cooling member and allowing movement of the heating member and the cooling member relative to each other. The sleeve, the first contact surface, and the second contact surface cooperatively form a cavity for receiving a fluid material to be measured. The platform is configured for controlling the relative movement of the heating member and the cooling member to adjust the length of the cavity. The fluid pressure assembly is configured for containing the fluid material and compressing the fluid material into the cavity. The manometer is disposed in one of the cavity and the fluid pressure assembly. The manometer is configured for detecting a fluid pressure of the fluid material in the cavity.

A method includes the steps of: (a) providing a measuring assembly comprising a heating member defining a first contact surface, a cooling member defining a second contact surface disposed facing the first contact surface, and a sleeve configured for joining the heating member and the cooling member and allowing movement of the heating member and the cooling member relative to each other, the sleeve, the first contact surface, and the second contact surface cooperatively forming a cavity; (b) compressing an amount of the fluid material into the cavity and maintaining a pressure of the fluid material subjected to arrive at a predetermined pressure valve; (c) providing a heat flux flowing through said amount of fluid material by the heating member and the cooling member; (d) measuring temperatures of the heating member and the cooling member; and (e) modulating length of the cavity in the heat transfer direction and performing steps (b), (c), and (d) again at least once; (f) determining the heat transfer characteristics of the fluid material.

Other advantages and novel features will be drawn from the following detailed description of preferred embodiments when conjunction with the attached drawings, in which:

BRIEF DESCRIPTION OF THE DRAWINGS

Many aspects of the present device can be better understood with reference to the following drawings. The components in the drawings are not necessarily drawn to scale, the emphasis instead being placed upon clearly illustrating the principles of the present device. Moreover, in the drawings, like reference numerals designate corresponding parts throughout the several views.

DETAILED DESCRIPTION OF THE PREFERRED EMBODIMENTS

Embodiments of the present invention will now be described in detail below and with reference to the drawings.

Figure 1:
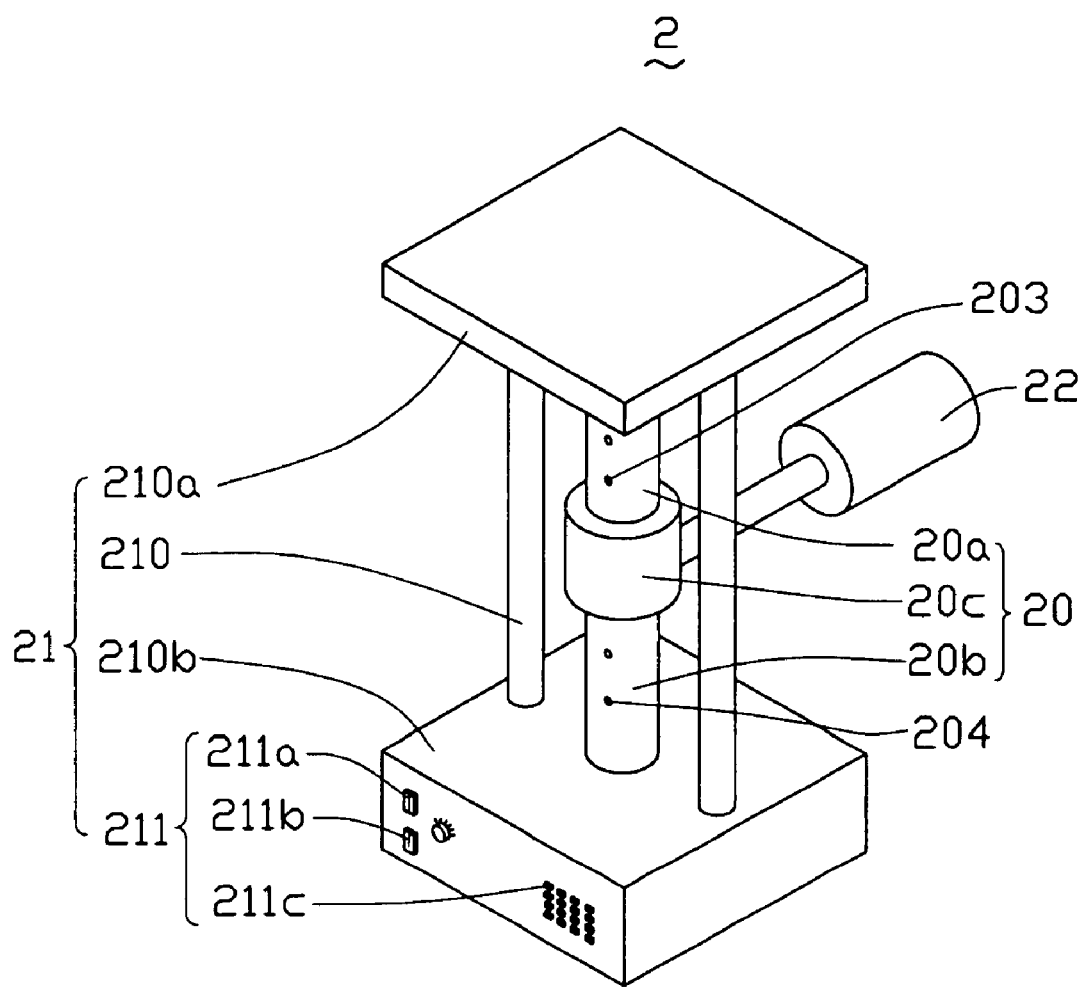
FIG. 1 is a schematic, isometric view of a device for measuring heat transfer characteristics of a fluid material according to a preferred embodiment.
Figure 2:
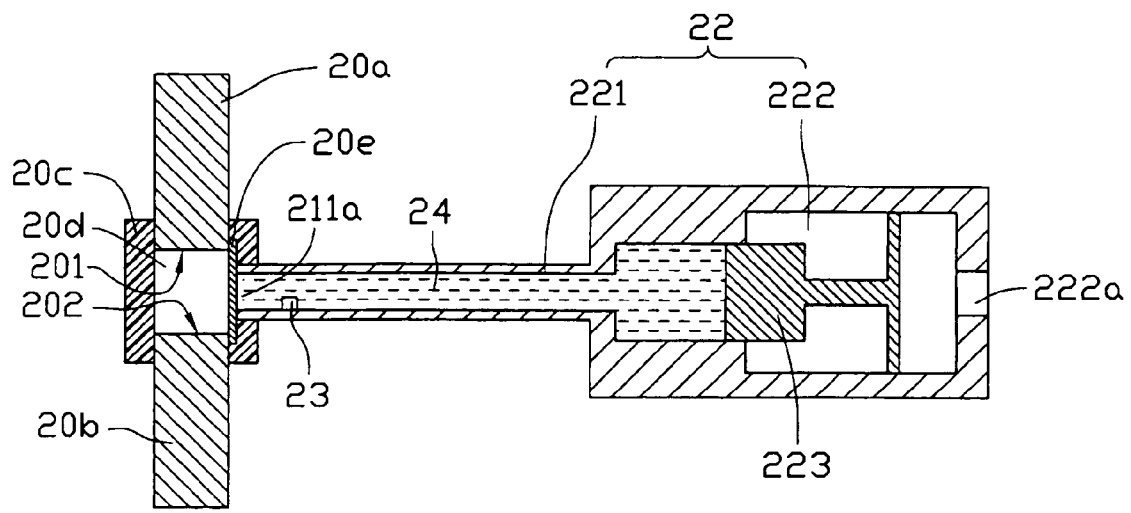
FIG. 2 is a schematic, partially cross sectional view of the device of FIG. 1, showing a measuring assembly and a fluid pressure assembly.

FIGS. 1 and 2 illustrate a device 2 in accordance with a first preferred embodiment. The device 2 mainly includes a measuring assembly 20, a fluid pressure assembly 22, a manometer 23, and a platform 21. The measuring assembly 20 is secured to the platform 21.

The measuring assembly 20 includes a heating member 20a defining a first contact surface 201, a cooling member 20b defining a second contact surface 202, and a sleeve 20c. The sleeve 20c connects the heating member 20a and the cooling member 20b. The second contact surface 202 is disposed facing the first contact surface 201. The first contact surface 201 and the second contact surface 202 are advantageously perpendicular to a heat transfer direction. The sleeve 20c is configured for hermetically adjoining the heating member 20a and the cooling member 20b, and allowing movement of the heating member 20a and the cooling member 20b relative to each other. The sleeve 20c, the first contact surface 201, and the second contact surface 202 cooperatively form a cavity 20d, for receiving an amount of fluid material 24 to be measured therein. The sleeve 20c is advantageously made of an adiabatic material, for example, asbestos, bakelite, polyurethane foam, glass wool, or expanded polystyrene. The cavity 20d advantageously has a uniform cross section in a heat transfer direction of the fluid material 24.

The heating and cooling members 20a and 20b define a plurality of first orifices 203 and a plurality of second orifices 204 therein. In practical measuring operation, a plurality of thermal probes (not shown) may be inserted into the first and second orifices 203 and 204, respectively. Each thermal probe inserted into a respective orifice is advantageously subjected to pressure to ensure close contact with the heating and cooling members 20a and 20b, thereby accurately measuring respective temperature of the heating and cooling members 20a and 20b where each thermal probe is positioned. Preferably, the first and second orifices 203 and 204 are linearly arranged at the heating and cooling members 20a and 20b along the heat transfer direction in uniform intervals, respectively.

The heating and cooling members 20a and 20b are advantageously made of a thermal conductive material, for example, copper, aluminum, silver, gold, or their combinations. The thermal conductive material advantageously has a melting point greater than that of the fluid material 24. Preferably, the heating and cooling members 20a and 20b each are an axial symmetrical structure such as, a cylindrical block or a cube-like block. The two members 20a and 20b advantageously have a common axis and a uniform cross section in the common axis. In the illustrated embodiment, the heating member 20a and the cooling member 20b each form cylindrical blocks. Thus, the heat transfer direction is essentially parallel to the common axis of the heating and cooling members 20a and 20b.

The fluid pressure assembly 22 is configured for containing the fluid material 24 and compressing the fluid material 24 into the measuring assembly 20. The fluid pressure assembly 22 includes a fluid chamber 221, a pressure chamber 222, and a piston 223 located between the fluid chamber 221 and the pressure chamber 222. The fluid chamber 221 contains the fluid material 24 to be measure and has an opening 221a communicating with the cavity 20d. The pressure chamber 222 is adjacent to the fluid chamber 221. The pressure chamber 222 advantageously defines an opening 222a communicating with a compressor, for driving the piston 223 to compress the fluid material 24 in the fluid chamber 221. In another embodiment, the piston 223 can be directly pushed by, for example, a manual force or a machine force. Advantageously, a valve 20e is disposed in the opening 221a of the fluid chamber 221, for controlling entrance of the fluid material 24 into the cavity 20 d from the opening 221a. The valve 20e is advantageously made of an adiabatic material, such as, for example, asbestos, bakelite, polyurethane foam, glass wool, or expanded polystyrene.

When the fluid material 24 is compressed into the cavity 20d, the fluid material 24 subjected to a predetermined pressure from the heating and cooling member 20a and 20b in order to ensure closely contact between the fluid material 24 and the heating and cooling member 20a and 20b. The manometer 23 is advantageously attached to the fluid chamber 221 and is in communication with the fluid chamber 221, measuring the fluid pressure of the fluid material 24 in the cavity 20d. The manometer 23 can facilitate accurately detect the pressure. Alternatively, the manometer 23 could be attached to the sleeve 20c, and in communication with the fluid material 24 in the cavity 20d, for directly measuring the predetermined pressure.

The platform 21 includes an upper substrate 210a, a lower substrate 210b, two retractable poles 210, and a controller 211. The upper substrate 210a is firmly connected with a distal end of the heating member 20a relative to the first contact surface 201. The lower substrate 210b can be firmly connected with a distal end of the cooling member 20b relative to the second contact surface 202. The two retractable poles 210 are advantageously interposed between the upper and lower substrates 210a and 210b. The two retractable poles 210 are advantageously parallel to the common axis of the heating member 20a and the cooling member 20b. Alternatively, one, three, or more retractable poles could be interposed between the upper and lower substrates 210a and 210b and be parallel to the common axis of the heating member 20a and the cooling member 20b.

The controller 211 is advantageously disposed on the lower substrate 210b and is configured for controlling retractable movement of the two retractable poles 210, thereby allowing a relative movement of the upper and lower substrates 210a and 210b. The relative movement of the upper and lower substrates 210a and 210b can bring out another corresponding relative movement of the heating member 20a and the cooling member 20b, thereby adjusting the length of the cavity 20d disposed between the heating and cooling members 20a and 20b, namely, the length of the fluid material 24 disposed between the first and second contact surface 201 and 202. Alternatively, the controller 211 could be disposed on the upper substrate 210a.

The controller 211 includes an upward button 211a, a downward button 211b, and a digital monitor 211c. The upward button 211a can be pressed to extend the two retractable poles 210. The downward button 211a can be pressed to retract the two retractable poles 210. The digital monitor 211c is configured for displaying the length data of the cavity 20d, which is depend on retractable movement of the retractable poles 210.

The measuring operation of the device 2 above-described mainly includes the steps of: compressing an amount of the fluid material into the cavity and maintaining a pressure of the fluid material subjected to arrive a predetermined pressure valve; providing a heat flux flowing through said amount of the fluid material by the heating member and the cooling member; measuring temperatures of the heating member and the cooling member; modulating length of the cavity in the heat transfer direction and performing three steps above-mentioned again at least once; and determining the heat transfer characteristics of the fluid material. The embodiment processes of the measuring operation of the device 2 are described as follows.

Initially, the valve 20e is opened to allow the fluid material 24 of the fluid chamber 221 to be compressed into the cavity 20d by the piston 223. The fluid material 24 compressed into the cavity 20d is advantageously subjected to a predetermined constant pressure during following measuring operations in order to obtain constant close contact between the fluid material 24 and the two members 20a and 20b. The constant pressure can be provided by the upper and/or lower substrates 210a/210b compressing the heating member 20a and the cooling member 20b under the control of the controller 211. The manometer 23 simultaneously detects fluid pressure of the fluid material. When the pressure detected is constant the valve 20e is closed. At the same time, the digital monitor 211c of the controller 211 shows a first length L1, which is also a length of the fluid material 24 compressed into the cavity 20d in the heat transfer direction. The fluid material 24 compressed into the cavity 20d is heated by the heating member 20a, and then transfers heat to the cooling member 20b. During the heat transfer process, a plurality of thermal probes are inserted into the first and second orifices 203 and 204, respectively, for measuring temperature where each thermal probe is positioned.

After a certain time, the temperatures measured by the thermal probes are stable. Surface temperatures $T_1$ and $T_2$ on the first and second contact surface 201 and 202 can be calculated based on the measured temperatures by the thermal probes. Heat flux Q is obtained based on an output power of the heating member 20a. Due to the heating and cooling member 20a and 20b each have a uniform cross section in the common axis, cross sectional area A in the heat transfer direction is essentially equal to cross sectional area of the heating member 20a or the cooling member 20b. As such, a first total heat resistance R1 between the first contact surface 201 and the second contact surface 202 can be calculated by the equation (1) as follows:

$$R1 = \frac{(T_1 - T_2)}{Q}. \tag{1}$$

After obtaining the first total heat resistance R1, a second, third, and forth total heat resistances R2, R3, R4 can be obtained by performing above-mentioned measuring operations based on different lengths L2, L3, L4 of the cavity 20d or the fluid material 24 in the cavity 20d. The different lengths L2, L3, L4 are adjusted by controlling the movement of the retractable poles 210 via the controller 211 and compressing the fluid material 24 into the cavity 20d via the piston 223.

Each total heat resistance R includes a heat resistance of the fluid material 24 in the cavity 20d and heat resistance $R_c$ between the fluid material and the first and second contact surface 201 and 202, as represented by the equation (3) as follows:

$$R = \frac{L}{A \times K} + R_c, \tag{3}$$

wherein L is a heat transfer length, namely the length of the cavity or length of fluid material in the heat transfer direction; A is a cross sectional area in the heat transfer direction, namely a cross sectional area of the heating member 20a or the cooling member 20b; K is thermal conductivity of the fluid material; and $R_c$ is heat resistance between the fluid material 24 and the first and second contact surface 201 and 202.

Figure 3:
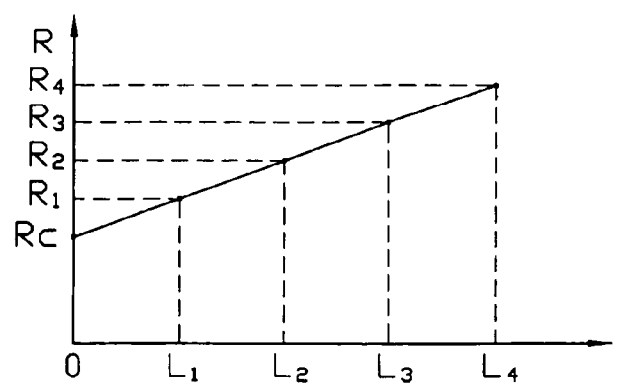
FIG. 3 is a graph of a relationship of total heat resistances and lengths of the fluid received in a cavity of the device of FIG. 1.

FIG. 3 shows a relationship graph of total heat resistances R and different lengths L1, L2, L3, L4 of the cavity 20d, respectively. In different measuring operations, A and K in the equation (3) are constant, therefore, the equation (3) is actually a linear equation, namely, the total heat resistance R depends on the heat transfer length L in a linear relationship. As such, while taking lengths L1, L2, L3, L4 as X-coordinate values and total heat resistances R1, R2, R3, R4 as Y-coordinate values, a line will thereby be obtained, as shown in FIG. 3. Accordingly, $R_c$ (i.e. the y-intercept) can be concluded by a linear regression analysis from the line in FIG. 3. The heat conductivity K can thereby be calculated from the equation (3) based on four groups of data obtained above, namely, R1-R4, L1-L4, A, and $R_c$.

Moreover, it is to be noted that although four groups of data about R and L are exemplarily illustrated herein, more data may be optionally selected in the application of the practical measuring operation by those skilled in the art.

It will be understood that the above particular embodiments and methods are shown and described by way of illustration only. The principles and features of the present invention may be employed in various and numerous embodiments thereof without departing from the scope of the invention as claimed. The above-described embodiments illustrate the scope of the invention but do not restrict the scope of the invention.

What is claimed is:

1. A device for measuring heat transfer characteristics of a fluid material, the device comprising:
   a measuring assembly comprising:
   a heating member defining a first contact surface;

a cooling member defining a second contact surface, the second contact surface disposed facing the first contact surface; and a sleeve being configured for hermetically adjoining the heating member and the cooling member, and allowing movement of the heating member and the cooling member relative to each other, the sleeve, the first contact surface, and the second contact surface cooperatively forming a cavity for receiving an amount of fluid material to be measured;

a platform configured for controlling the relative movement of the heating member and the cooling member to adjust the length of the cavity;

a fluid pressure assembly being configured for containing the fluid material and compressing the fluid material into the cavity; and a manometer attached to and directly in communication with one of the sleeve and the fluid pressure assembly, the manometer being configured for detecting fluid pressure of the fluid material in the cavity.

2. The device as claimed in claim 1, wherein the heating member and the cooling member each are made of a thermally conductive material selected from the group consisting of copper, aluminum, silver, gold, and their combinations.

3. The device as claimed in claim 1, wherein facing ends of the heating member and the cooling member are slidably received in the sleeve.

4. The device as claimed in claim 1, wherein the platform comprises two substrates which are both firmly connected with a distal end of the heating member relative to the first contact surface and a distal end of the cooling member relative to the second contact surface, and at least one retractable pole connected between the two substrates.

5. The device as claimed in claim 4, wherein a controller is disposed on one of the two substrates, the controller being configured for controlling the retractable movement of the at least one retractable pole.

6. The device as claimed in claim 1, wherein the heating member and the cooling member have a common axis and a uniform cross section in the common axis, the common axis being essentially parallel to a heat transfer direction of the fluid material.

7. The device as claimed in claim 6, wherein the heating member and the cooling member each define a plurality of orifices, a plurality of thermal probes each being inserted into a respective orifice, for measuring respective temperature where each thermal probe is positioned.

8. The device as claimed in claim 7, wherein the orifices are linearly arranged along the hear transfer direction at uniform intervals.

9. The device as claimed in claim 1, wherein the fluid pressure assembly comprises a fluid chamber having an opening communicating with the cavity, a pressure chamber connected with the fluid chamber, and a piston interposed between the fluid chamber and the pressure chamber, the fluid chamber containing the fluid material to be measured, the piston being configured for compressing the fluid material in the fluid chamber into the cavity by pressure from the pressure chamber.

10. The device as claimed in claim 9, wherein a valve is disposed at the opening of the fluid chamber, for controlling entrance of the fluid material into the cavity from the opening of the fluid chamber.

11. The device as claimed in claim 10, wherein the valve and the sleeve are made of an adiabatic material.

12. A device for measuring heat transfer characteristics of a fluid material, the device comprising:

a heating member;

a cooling member spaced from the heating member;

an adjoining member, wherein facing ends of the heating member and the cooling member are slidably received in the adjoining member and the adjoining member thereby hermetically adjoins the heating member and the cooling member with a hermetical cavity formed therebetween, the cavity is configured for containing an amount of the fluid material which contacts the heating member and the cooling member and is capable of transferring heat from the heating member to the cooling member in a heat transfer direction, and a length of the cavity in the heat transfer direction is changeable by relative movement of the heating member and the cooling member; and a fluid pressure assembly configured for flowing said amount of the fluid material into the cavity.

13. The device as claimed in claim 12, further comprising a pressure detecting member configured for detecting a pressure of the fluid material in the cavity.

14. The device as claimed in claim 12, wherein a valve is disposed between the fluid pressure assembly and the cavity, the valve and the adjoining member being made of adiabatic material.

15. The device as claimed in claim 12, wherein the cavity has a uniform cross section in the heat transfer direction.

* * * * *